(12) United States Patent
Clancy et al.

(10) Patent No.: US 8,637,051 B2
(45) Date of Patent: Jan. 28, 2014

(54) COMPOSITIONS AND METHODS FOR TREATMENT OF MUCOSAL INFECTIONS

(75) Inventors: Robert Llewellyn Clancy, Newcastle (AU); Gerald Pang, New South Wales (AU); Margaret Lorraine Dunkley, New South Wales (AU)

(73) Assignee: Hunter Immunology Limited, Sydney (AU)

( * ) Notice: Subject to any disclaimer, the term of this patent is extended or adjusted under 35 U.S.C. 154(b) by 271 days.

(21) Appl. No.: 10/276,829

(22) PCT Filed: May 21, 2001

(86) PCT No.: PCT/AU01/00588
§ 371 (c)(1),
(2), (4) Date: May 22, 2003

(87) PCT Pub. No.: WO01/87332
PCT Pub. Date: Nov. 22, 2001

(65) Prior Publication Data
US 2004/0057965 A1    Mar. 25, 2004

(30) Foreign Application Priority Data

May 19, 2000  (AU) ...................................... PQ7612

(51) Int. Cl.
*A61K 39/102* (2006.01)
*A61K 39/00* (2006.01)
*A61K 45/00* (2006.01)
*A01N 63/00* (2006.01)

(52) U.S. Cl.
USPC .................. 424/256.1; 424/184.1; 424/278.1; 424/93.45; 424/93.4

(58) Field of Classification Search
USPC .......................... 424/203.1, 9.2, 184.1, 278.1
See application file for complete search history.

(56) References Cited

U.S. PATENT DOCUMENTS

| | | | | |
|---|---|---|---|---|
| 7,223,398 B1 * | 5/2007 | Tuck et al. | ................. | 424/184.1 |
| 2002/0044926 A1 * | 4/2002 | Reid et al. | ................. | 424/93.45 |

FOREIGN PATENT DOCUMENTS

| | | |
|---|---|---|
| WO | WO 97/45139 | 12/1997 |
| WO | WO 98/56415 | 12/1998 |
| WO | WO 99/12416 | 3/1999 |
| WO | WO 99/32137 | 7/1999 |
| WO | WO 99/32634 | 7/1999 |
| WO | WO 99/33868 | 7/1999 |
| WO | WO 99/38529 | * 8/1999 |
| WO | WO 99/40188 | 8/1999 |
| WO | WO 99/43349 | * 9/1999 |
| WO | WO 99/44634 | * 9/1999 |
| WO | WO 99/44635 | 9/1999 |
| WO | WO 00/06694 | 2/2000 |
| WO | WO 00/62801 | 10/2000 |

OTHER PUBLICATIONS

Isolauri et al (Improved immunogenicity of oral D x RRV reassortant rotavirus vaccine by *Lactobacillus casei* GG, Vaccine, 1995; 13(3): 310-12).*

Walduck et al (Biodegradable implants for the delivery of veterinary vaccines: design, manufacture, and antibody reponses in sheep, Journal of Controlled Release, 1998; 51: 269-280).*

Aebischer et al (Subunit vaccination of mice against new world cutaneous Leishmaniasis: comparison of three protein expressed in Amastigotes and six adjuvants, Infection and Immunity, 2000;68(3): 1328-1336).*

Maassen (Orally administered *Lactobacillus* strains differentially affect the direction and efficacy of the immune response, The Veterinary Quarterly, 1998; 20(sup. 3): S81-S83).*

Claassen et al (New and Safe "Oral" Live Vaccines Based on *Lactobacillus*, Adv. Exp. Med. Biol, 1995; 371B: 1553-8).*

Respiratory Tract Infections (RTI's), ( www.merck.com , p. 1-3).*

Boslego et al (Gonorrhea Vaccines, Chapter 17, 211-223).*

Ellis (New technologies for making vaccines, text book, 1998: 568-575).*

Christina von Hunolstein, et al. *Synthetic oligodeoxynucleotide containing CpG motif induces an anti-polysaccharide type 1-like immune response after immunization of mice with Haemophilus influenzae type b conjugate vaccine*. International Immunology 12(3):295-303, 2000.

Isabelle Rauly, et al. *Carrier Properties of a Protein Derived from Outer Membrane Protein A of Klebsiella pneumoniae*. Infection and Immunity 67(11):5547-5551, Nov. 1999.

E. Claassen et al. "New and Safe Oral Live Vaccines on Lactobacillus". Advances in Experimental Medicine and Biology 371B:1553-1558, 1995. XP009022349.

E. Isolauri et al. "Improved immunogenicity of oral D x RRV reassortant rotavirus vaccine by *Lactobacillus casei* GG". Vaccine 13(3):310-312, 1995. XP004057672.

C. B. M. Maassen et al. "Orally Administered *Lactobacillus* Strains Differentially Affect the Direction and Efficacy of the Immune Response". The Veterinary Quarterly 20(Supp. 3):S81-S83, 1998. XP001203950.

E. Medina et al. "Modulation of immune responses following antigen administration by mucosal route". FEMS Immunology and Medical Microbiology 27(4):305-311, Apr. 2000. XP002307833.

P. H. Pouwels et al. "Lactic acid bacteria as antigen delivery vehicles for oral immunization purposes". International Journal of Food Microbiology 41:155-167, 1998. XP000921209.

A. Stjernquist-Desatnik et al. "Protective effect of heterologous Gram-positive vaccine against lethal upper respiratory tract infection with type M50 group A streptococci in mice". Vaccine 8(2):150-152, Apr. 1990.

J. M. Wells et al. "Lactic acid bacteria as vaccine delivery vehicles". Antonie Van Leeuwenhoek 70(2-4):317-330, Oct. 1996. XP000914879.

* cited by examiner

*Primary Examiner* — Vanessa L Ford
*Assistant Examiner* — Lakia Tongue
(74) *Attorney, Agent, or Firm* — Raymond Van Dyke; Van Dyke Law

(57) ABSTRACT

The present invention is concerned with novel compositions and vaccines useful for prophylactic an/or therapeutic treatment of mucosal infections, and in particular it is concerned with oral vaccines and with methods of enhancing mucosal resistance to infection or for treating established infections, of the respiratory tract.

27 Claims, 1 Drawing Sheet

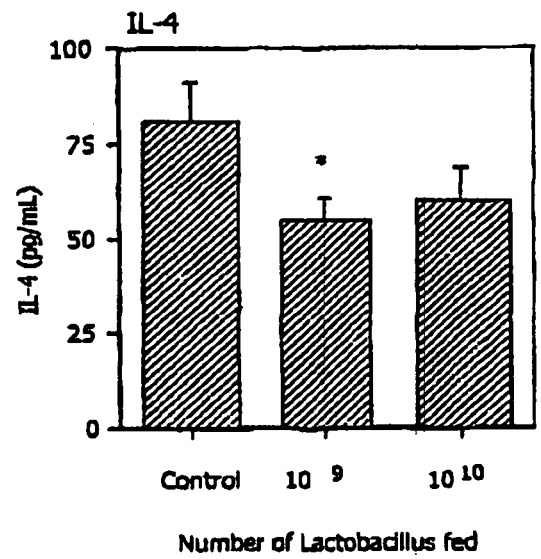
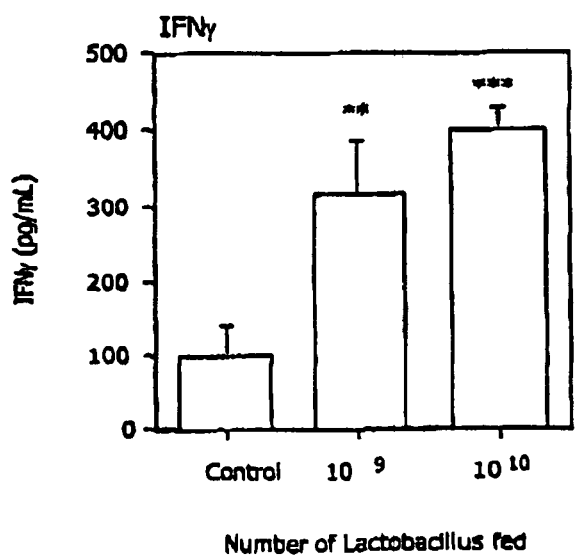
* p<0.05,  p<0.01, *p<0.001

COMPOSITIONS AND METHODS FOR TREATMENT OF MUCOSAL INFECTIONS

TECHNICAL FIELD

The present invention is concerned with novel vaccine compositions that induce mucosal protection and in particular to oral vaccines and to methods of enhancing mucosal resistance to infection or for treating established infections.

BACKGROUND ART

Endobronchitis has been used as a model of mucosal immunology and more specifically to reflect a particular balance of the host-parasite relationship at the mucosal surface. The normally sterile bronchus mucosa becomes colonised by "avirulent" bacteria which do not generally invade. Most prominent is non-typable *Haemophilus influenzae* (NTHI). Acute episodes of infection in subjects with chronic lung disease are thus likely to be initiated by events which disturb a finely balanced relationship between colonising bacteria and the bronchus mucosa. The restraining host response involves Th1 T cells (which produce γ interferon), which operate by recruiting and activating neutrophils within the bronchus mucosa. If excessive and/or inappropriate, this process leads to increase cough and purulent sputum, the hallmark of "acute bronchitis" in subjects with established chronic lung disease.

The original oral vaccine used killed NTHI to activate the common mucosal system to enhance release of lymphocytes (then considered to be antibody producing B lymphocytes) from the Payer's patches along the small intestine, which relocated within the bronchus mucosa, producing IgA antibody which would prevent descent of bacteria into the bronchi. This concept has been superseded. This vaccine requires that (i) a single bacterial content and (ii) no added adjuvant. The absence of adjuvant was thought necessary to avoid the then considered restrictions imposed by the highly down-regulated mucosal environment, ie additions of adjuvant to a simple single bacterial vaccine would enhance mucosal downregulation, reduce vaccine effectiveness, and even promote or exacerbate infection.

It is an object of the present invention to overcome or at least ameliorate one or more of the limitations of the prior art or to provide a useful alternative.

SUMMARY OF THE INVENTION

According to a first aspect there is provided a mucosally administrable composition comprising one or more antigens derived from at least one microorganism which is capable of causing infection at a mucosal surface and an adjuvant capable of inducing a Th1 cellular immune response, wherein the adjuvant is not derived from a microorganism capable of causing infection at a mucosal surface.

Preferably the antigen is derived from a bacterium, a fungus or a virus. Even more preferred is that the antigen is represented by the whole microorganism. As a further preference, when the antigen is a whole microorganism, it is a killed microorganism however it will be understood that live or live attenuated microorganisms may also be used effectively. It will also be understood however, that individual antigens or homogenates and sonicates of microorganisms can also be used with the expectation of achieving similar results.

Particularly preferred are respiratory tract bacterial and fungal pathogens or those normally colonising the respiratory tract and having the potential to cause infection, for example NTHI, *Pseudomonas aeruginosa, Streptococcus pneurnoniae, Staphylococcus tabus, Staphylococcus aureus* and the like, singularly or in combination.

The compositions of the present invention are intended to be administered orally and thus may be combined with the known pharmaceutically acceptable, carriers, solvents and excipients.

Preferably the adjuvant used in the compositions of the present invention is a microorganism or a part thereof which is not. an organism that is capable of causing infection at a mucosal surface and which can induce a cellular immune response of the Th1 type. Also preferred is that the adjuvant is a bacterium, for example one which can be selected from, but not limited to, lactic acid bacteria, Mycobacterium species or Bifidobacterium species. Even more preferred is the use of *Lactobacillus acidophilus* (*L. acidophilus*), *Lactobacillus ferment*(*L. fermentum*) or *Mycobacterium vaccae* (*M vaccae*), or parts thereof which are capable of inducing the Th1 cellular response. Specially preferred is *L. acidophilus*. *L. acidophilus, L. fermentum* or *M. vaccae* may be used live or as an inactivated preparation, as long as they are capable of inducing the Th1 response. For preference *L. acidophilus* and *L. fermentum* is used as a live preparation. It is considered that other bacteria would also be suitable as adjuvants (whether they have probiotic effect or not), for example the well known adjuvating bacteria such as for example *L. casei, L. Plantarum, L. rhamnosus, Bifidobecterium breve* and the like. The use of probiotic bacteria as adjuvants is preferred.

Additional known conventional adjuvants may also be included. A range of suitable pharmaceutical adjuvants, excipients and carriers, and methods of preparing suitable formulations, would be well known to those skilled in the field of pharmaceutical formulation, and details of such adjuvants, excipients and carriers can be found in standard texts and manuals, such as for example "Remington: The Science and Practice of Pharmacy (Mack Publishing Co., 1995) which is incorporated in its entirety herein by reference. Further, the compositions of the present invention may be in the form of a food product or a food supplement, such as for example a dairy product or supplement. The methods of preparation of such products and supplements would also be clear to those skilled in the art, as they are well known procedures and processes, particularly those concerning the production of for example yoghurts and other milk products.

According to a second aspect of the present invention there is provided a vaccine comprising the composition according to the first aspect According to a third aspect there is provided a method of therapeutic or prophylactic treatment of a mucosal infection comprising the administration to a subject requiring such treatment a composition according to the first aspect or a vaccine according to the second aspect It will be understood however that a subject requiring treatment, whether prophylactic or therapeutic, may be administered initially only a part of the composition, for example the adjuvant in the form of bacteria such as *L acidophilus* and *L. fermentum*, followed thereafter by the administration of the antigen or antigens intended to ultimately provide specific immunity to the potential pathogen. The initial treatment with the adjuvant may take the form of a single bolus dose but may also, and for preference, be administered in repeated doses for a period of time before the antigen is administered. The administration of the adjuvant may also continue after cessation of antigen administration.

As it is now clear that the mucosal immune system is common to all mucosal surfaces, the compositions and vaccines of the present invention can be applied to any potential mucosal pathogen and any mucosal surface, including but not limited to bucal cavity, the respiratory tract and the intestinal tract.

Preferably the compositions or vaccines of the present invention are administered orally but application to any mucosal surface, for example the mucosa of the respiratory tract or mucosa of the intestinal tract, is contemplated.

The compositions and vaccines of the present invention are advantageously used to induce mucosal protection against infection however they can also be used as prophylactics in the treatment of existing bacterial, fungal and/or viral mucosal infections. Further, the preferred use of the compositions and vaccines of the present invention is when the mucosal surfaces are already colonised by bacteria.

Thus according to a fourth aspect there is provided a method of therapeutic or prophylactic treatment of a mucosal infection comprising the administration to a subject requiring such treatment the adjuvant part of a composition according to the first aspect, followed by the antigen part of a composition according to the first aspect.

Preferably the treatment with the adjuvant part is by administration of a single bolus dose of adjuvant however treatment with the adjuvant part can also be by administration of repeated doses of adjuvant. More preferred however, is that the adjuvant and the antigen are co-administered.

In a flutter embodiment of the invention, where the adjuvant is administered before or together with the antigen, the administration of the adjuvant may continue after the administration of the antigen part.

The compositions and vaccines of the present invention may be administered to any mucosal surface and have the desired effect because of the common mucosal immune system. Preferred mucosal surfaces bucal cavity, the respiratory tract and the intestinal tract, however, as mentioned above, it will be understood by those skilled in this field that administration to any mucosal surface would be effective.

Preferably the compositions or the vaccines are administered orally.

Preferably, the vaccine is administered in two courses, followed by a booster course.

The preferred dosage of the adjuvant, when the adjuvant is a whole live probiotic bacterium, is from about $1 \times 10^3$ to about $1 \times 10^{12}$ organisms.

The preferred dosage of the antigen, when the antigen is represented by a whole killed microorganism, is from about $1 \times 10^3$ to about $1 \times 10^{12}$ organisms. More preferred is a dosage wherein the ratio of whole killed microorganisms (antigen) to probiotic bacteria (adjuvant) is about 5:1 or greater.

Also preferred is the administration of the compositions or the vaccines, each year before outbreak of seasonal infections.

BRIEF DESCRIPTION OF THE FIGURE

FIG. 1: IL-4 and IFN-γ production following feeding with *Lactobacillus acidophilus*

DESCRIPTION OF THE PREFERRED EMBODIMENTS

It has been surprisingly found that by combining, for example, a specific antigen relevant to mucosal infection (eg whole bacteria such as *Haemophilus influenzae*) and non-specific bacteria, ie. those that are not normally associated with mucosal infection, protracted protection against mucosal infection can be achieved. Without wishing to be bound by any particular mechanism of action, the present invention is based on the notion that the non-specific bacteria used induce T cells to produce a particular cytokine response which amplifies the protection otherwise expected from administration of traditional vaccine preparations. More specifically, but again not wishing to be bound by any particular mechanism of action, it is thought that by the administration of non-specific bacteria the mucosal immune system is being biased towards the Th1 (ie IFN-γ) end of the T cell response spectrum. It is considered that the Th1 response best controls mucosal colonisation. The use of such organisms, and other adjuvants capable of stimulating a Th1 response, determines a Th1 response that is detectable and can have effects distant from the site of administration.

It is demonstated herein that a non-specific bacteria such as lactic acid bacteria, have the capacity to downregulate IL-4 and to enhance IFN-γ production in a highly "Th2-biased" murine model (see Example 1). It is also demonstated herein that a non-specific bacterium such as lactobacillus provides additive protection in a rat model of non-typale *Haemophilus influenzae* (HTHI) clearance from the bronchus (shown in involve CD4 T cells, with no antibody) see Example 2).

The animal model used by way of example in th epresent studises is a model of conlonisaiton, relevant to both therapy and prevention of infection. Colonisation is an essential determinant for infection and the model has been used in the context of other therapeutic and prophylactic vaccines to establish efficacy, dosage protocols and the like.

In a particular embodiment of the present inveniton a therpeutic oral vaccine conbines: 1) specific bacteria which are found within the respiratory tact, singly or in combination (for example, but not limited to, MTHI, *S. pneumoniae, Ps. asruginosa, S. albus, S. aureus*), as killed or live bacteria, and 2) non-specific bacteria (also referred to herein as probiotic bacteria), which have the capacity to switch nucosal immunity in the directionof a Th1 T cell response (may also be used killed or live), for example, but not limited to, Lactobacillus species (eg. *L. acidophilus*) and/or Mycobacterium species, (eg *M. vaccae*).

This type of oral vaccine operates best when the mucsal surface is already colonised (as thses bacteria re-stimulate newly relocated cells within the mucosa) ie functions as a therapeutic vaccine. it can, however, function as a proghylactic vaccine.

To avoid inactivation of bacteria by gastric, enteric coated capsules (or similar) may be used to release the bacterial contents along the small intestine. Another option is longer term use of the non-specific bacteria to create a more durable Th1 mucosal envirnment, prior to the administration of the specific antigen(s) or bacteria intended to induce a specific immune response against the potential mucasal pathogen. The 'non-specific' bacteria alone do not induce specific protection.

The non-specific bacteria also enhance repsonse to certain antigens given parenterally, particularly those influencing mucosal protection (by favouring a particular immune outcome).

A combination of Gran+ve bacteria as probiotic asjuvants has synergistic activity in this system and is also comtemplated herein. Various respiratory mucosal surfaces can be protected as the mucosal immune system is common to all mucosal surfaces (eg bronchus, sinus, and middle ear among others).

The invention will now be more particularly described with reference to specific, non-limiting, examples.

EXAMPLE 1

Effect of probiotic bacteria on Th1/Th2 cytokine response

To determine whether probiotic bacteria down-regulate Th2 and up-regulate Th1 cytokine response, C57/B16 mice were fed intragastrically using a feeding needle, various numbers of *Lactobacillus acidophilus* (obtained from University of New South Wales, School of Mircobiology and Immunology Culture Collection, Sydney, Australia) on (OVA) and aluminium hydroxide in 0.2 mL phosphate-buffered saline administered by peritoneal injection. The mice were further fed ten times with *L. acidophilus* every two days for two weeks before they were sacrificed. Lymphocytes were isolated by teasing spleens through a sieve, washed with PBS, and resuspended at $10 \times 10^6$. One mL aliquots of the cell suspension were dispensed into wells of a 24-well flat-bottomed microtitre plate and stimulated with OVA (5 μg/mL). After incubation for 4 days the supernatants were collected and assayed for IL-4 and IFN-γ production by standard ELISA techniques using IL-4 or IFN-γ monclonal antibody pairs.

Briefly, wells of a 24-well microtitre plate were coated with a capture anti-IL-4 antibody. After incubation at room temperature for 1 hr, the wells were washed and biotinylated anti-IL-4 antibody was added to each well. Following incubation for a further 1 hr, the wells were washed and streptavidin peroxidase conjugate as added to each well. After incubation for 30 mins, the wells were washed and then TMB substrate was added. The colour development was read at 450/620 nm in an ELISA plate reader. The level of IL-4 in unknown samples was quantitated by intrapolation using a standard curve. A similar procedure was used for measurement of IFN-γ.

The results shown in FIG. 1 A and B demonsrate that feeding *L. acidophilus*.resulted in the suppression of IL-4 production in dose-dependent manner(FIG. 1A) whereas the production of IFN-γ was enhanced (FIG 1B).

EXAMPLE 2

Enhanced Clearance of NTHi from the Respiratory Tract Induced by a Single Intra-Lumenal dose of live *L. acidophilus* and killed NIHi The capacity of *L. acidophilus* to enhance clearance of non-typeable H influenzae (NTHI) from the respiratory tract was investigated in a rat model.

DA rats (200-250 gm, 8-10 weeks old, Animal Resource Centre, Perth, WA were immunised by a single intra-humenal (IL) injection (into the lumen of the small intestine) of 0.75 mL of PBS containing $5 \times 10^9$ killed NTHi alone or in combination with $2.5 \times 10^{10}$ *L. acidophilus (as shown in Table 1)*. The IL dose was by direct injection into the intestinal lumen after exposing the duodenum by laparotomy. This considered equivalent to an enteric-coated dose (as may be prepared for humans) being released into the gut lumen affter oral ingestion. The rats were given an intra-tracheal (IT) boost with 50 μL of PBS alone (group A) or containing $5 \times 10^8$ killed NTHI in 50 μL of PBS. After 4 hrs, the rats were sacrificed and the total number of NTHI in bronchial lavage (BAL) and lung homogenate (LH) was determined by plating out serial 10-folk dilutions of the BAL or LH onto chocolate agar plates. Ater overnight incubation at 37° C. the number of colonies were counted. The total number of bacteria in BAL and LH, expressed as colony forming units (CFU), as shown in Table 2.

TABLE 1

| Rat groups: IL dose and IT boost | | |
|---|---|---|
| Group | IL dose | IT boost |
| A | PBS | PBS |
| B | NTHi | NTHi |
| C | NTHi/*L. acidophilus* | NTHi |
| D | *L. acidophilus* | NTHi |

TABLE 2

| Recovery of live NTHi from the respiratory tract (mean ± SEM) | | |
|---|---|---|
| Group | BAL CFU ($10^6$) | LH CFU ($10^6$) |
| A | 3.2 ± 1.1 | 19.4 ± 5.9 |
| B | 1.0 ± 0.3 | 19.2 ± 10.4 |
| C | 0.5 ± 0.3$^{a,c}$ | 3.3 ± 0.7$^{b,d}$ |
| D | 1.7 ± 0.3 | 25.9 ± 10.0 |

$^a$p = 0.034 compared with group A
$^b$p = 0.018 compared with group A
$^c$p = 0.264 compared with group B
$^d$p = 0.165 compared with group B
p < 0.05 is considered statistically significant
This data shows that the combination of killed NTHi and live *L. acidophilus* is more efficacious than NTHi alone or *L. acidophilus* alone.

EXAMPLE 3

Enhanced Clearance of NTHi from the lungs of Immunised Rats Fed *L. Acidophilus*

DA rat (200-250 gm, 8-10 weeks old, Animal Resource Centre, Perth, WA) were fed by gavage with $5 \times 10^{10}$ *L. acidophilus* in 1.0 mL PBS or PBS alone every 2 days for 7 days at which time the rats were immunised with formalin-killed NTHi ($5 \times 10^9$ per rat) administered intralumenally (IL) in 0.5 mL of PBS. Rats continued to be fed every 2 days for 2 weeks and were then boosted with 50 μL of PBS containing formalin killed NTHi ($5 \times 10^8$ per rat) administered by the intratracheal (IT) route. After feeding with *L. acidophilus* for a further 7 days, the raats were infected IT with 50 μL of PBS containing $5 \times 10^8$ live NTHi. After 4 hrs, levels of colonisation in the lung were determined in BAL and LH as described in Example 2. The immunization and feeding of the various groups is shown in Table 3. The bacterial recovery is shown in Table 4.

TABLE 3

| Rat groups: dosing regimens | | | |
|---|---|---|---|
| Group (5 rats per group) | Feed | IL dose | IT boost |
| A | Nil | PBS | PBS |
| B | Nil | NTHi | NTHi |
| C | *L. acidophilus* | PBS | PBS |
| D | *L. acidophilus* | NTHi | NTHi |

TABLE 4

Recovery of live NTHi from the lungs

| Group | BAL CFU ($10^6$/mL) | LH CFU ($10^6$/mL) |
|---|---|---|
| A | 25.9 ± 7.4 | 90.2 ± 29.0 |
| B | 4.6 ± 3.0[a] | 4.9 ± 1.2[b] |
| C | 0.7 ± 0.3[c] | 12.5 ± 5.7[d] |
| D | 0.2 ± 0.1[e,g] | 3.2 ± 2.0[f,h] |

[a] p = 0.011 compared with A
[b] p = 0.018 compared with A
[c] p = 0.043 compared with A
[d] p = 0.093 compared with A
[e] p = 0.018 compared with A
[f] p = 0.033 compared with A
[g] p = 0.235 compared with B
[h] statistically insignificant compared with B Rats fed *L. acidophilus* and immunised with killed NTHi were more resistant to infection by NTHi in the lungs than rats immunised with killed NTHi only or fed *L. acidophilus* only. Furthermore, rats fed by gavage with repeated doses of *L. acidophilus* were more resistant to infection than rats given a single bolus of *L. acidophilus* (example 2). Not wishing to be bound by any particular mechanism of action, this data suggestss that enhanced clearance may be due to increased colonisation in the gut with *L. acidophilus* following repeated feeding.

EXAMPLE 4

Intra-Lumenal Dosing with Killed NTHi and live *L. fermentum* Provides Enhanced Protection Against a Subsequent Acute NTHi infection The capacity of *L. fermentum* to enhance clearance of NTHi, either alone or in combination with killed NTHi was evaluated in a rat model of acute NTHi respiratoryl infection.

DA specific pathogen-free rats (177-200 g) were obtained from the Central Animal house, University of Newcastle, Newcastle, NSW). Groups of 5 rats were given a single injection into the gut lumen of the small intestine of 0.75 mL of PBS only or PBS containing either 5×10$^9$ killed NTHi only, plus 2.5×10$^{10}$ *L. fermentum*, or 2.5×10$^{10}$ *L. fermentum* only as shown in Table 5 below. On day 14, rats in group A were sham-boosted IT with 50 µL of PBS and rats in groups B-D were boosted with 50 µL of PBS containing 5×10$^8$ killed NTHi. On day 21 the rats were infected IT with 5×10$^8$ live NTHi in 50 µL of PBS. Four hours later rats were killed by an overdose fo pentobarbitone administered intra-peritoneally. The lungs were lavaged with 10 mL of PBS to obtain broncho-alveolar lavage fluid (BAL). The lungs were then homogenised in 10 mL f PBS to obtain lung homogenate (LH). The number of bacteria in BAL and LH was determined by performing serial dilution of BAL and LH and plating known volumes on chocolate agar plates. After overnight incubation at 37° C. the colonies were counted were counted and the total number of colony-forming units (CFU) in BAL and LH determined. The number of bacteria in each rat group is shown in Table 6.

TABLE 5

Rats (5 per group) were given a single intra-lumenal dose of various combinations of killed NTHi and live *L. fermentum* as follows:

| Rat group | IL immunization | IT boost |
|---|---|---|
| A | PBS | PBS |
| B | NTHi 5 × 10$^9$ | NTHi 5 × 10$^1$ |
| C | NTHi 5 × 10$^9$ + *L. fermentum* 2.5 × 10$^{10}$ | NTHi 5 × 10$^2$ |
| D | *L. fermentum* 2.5 × 10$^{10}$ | NTHi 5 × 10$^3$ |

TABLE 6

Recovery of live NTHi from the lung.

| Rat group | BAL CFU ($10^6$) | LH CFU ($10^6$) |
|---|---|---|
| A (5) | 3.67 ± 1.30 | 103.5 ± 34.2 |
| B (5) | 0.40 ± 0.22 P = 0.038* | 17.4 ± 6.8  P = 0.039* |
| C (5) | 0.27 ± 0.11 P = 0.032* | 5.7 ± 1.5  P = 0.021* |
| D (5) | 0.49 ± 0.19 P = 0.042* | 0.82 ± 0.37 P = 0.017* |

*compared to group A
Also, for LH B > D (P = 0.041), and C > D (P = 0.015).

This data suggests that *L. fermentum* slone or with killed NTHi has greater efficacy as a prophylactic against subsequent acute respiratory infection than does killed NTHi alone. Thus, this lactobacillus strain is also effective against acute respiratory infection.

EXAMPLE 5

Dose-Ranging Study of *L. acidophilus* Given with a Fixed NTHi Dose

DA specific pathogen-free rats (197-230 g) were obtained from the Central Animal house, University of Newcastle, Newcastle, NSW). Groups of 6 rats were given a single IL dose of PBS or a fixed dose of killed NTHi (5×10$^9$) plus one of various doses of live *L. acidophilus* as shown in Table 7 below. On day 14, rats in group A were sham-boosted with 50 µL of PBS and rats in groups B-D were boosted with 50 µL of PBS containing 5×10$^8$ killed NTHi. Boosting was by intra-tracheal delivery. On day 21 the rats were infected by intra-tracheal instillation of 5×10$^8$ live NTHi in 50 µL of PBS. Four hours later rats were killed by an overdose of pentobarbitone administered intra-peritoneally. The lungs were lavaged with 10 mL of PBS to obtain broncho-alveolar lavage fluid (BAL). The lungs were then homogenised in 10 mL of PBS to obtain lung homogenate (LH). The number of bacteria in BAL and LH was determining by performing serial dilution of BAL and LH and plating known volumes on chocolate agar plates. After overnight incubation at 37° C. the colonies were counted and the total number of colony-forming units (CFU) in BAL and LH determined The number of bacteria in each group is shown in Table 8.

TABLE 7

Rat groups: IL dosing and IT boosting

| Rat group | IL immunization | IT boost |
|---|---|---|
| A (6) | PBS | PBS |
| B (5) | NTHi + *L. acidophilus* 2 × 10$^8$ | NTHi |
| C (6) | NTHi + *L. acidophilus* 1 × 10$^9$ | NTHi |
| D (6) | NTHi + *L. acidophilus* 5 × 10$^9$ | NTHi |
| E (6) | NTHi + *L. acidophilus* 2.5 × 10$^{10}$ | NTHi |

TABLE 8

Recovery of live NTHi from the lung:

| Rat group | BAL CFU ($10^6$) | LH CFU ($10^6$) |
|---|---|---|
| A (6) | 1.96 ± 0.54 | 17.9 ± 4.5 |
| B (5) | 0.65 ± 0.46 | 3.3 ± 1.7 P = 0.021* |
| C (6) | 1.22 ± 0.49 | 4.7 ± 1.4 P = 0.019* |
| D (6) | 0.71 ± 0.22 | 6.8 ± 2.8 |
| E (6) | 3.75 ± 1.74 | 13.2 ± 5.2 |

*compared to group A.

The lower doses of lactobacillus are more effective than the higher doses. Again, without wishing to be bound by any particular mechanism of action, this dtata suggests that the 'adjuvant effect' may be operating differently from the lactobacillus-only effect.

From the above data the equivalent dosage for humans is likely to be of the order of $1 \times 10^8$ to $1 \times 10^{12}$ bacteria.

Example 6

Evaluation of Optical Dose-Size/Dose-Regimen for NTHi Immunization

The optical dose size and dosing regimen for killed NTHi immunization were determined. The different regimens evaluated are shown in Table 9. A single IL dose, a single IL dose followed by a gavage dose, and a single IL dose followed by two gavage doses were evaluated. Only one dose could be given IL as this involves surgery to expose the duodenum. Animal ethics considerations allow only one surgical intervention. Sebsequent dos s were therefore delivered by garage.

TABLE 9

Dosing regimens

| Regimen | Dose 1 (IL) | Dose 2 (Gavage) | Dose 3 (Gavage) | IT boost | Infection/kill |
|---|---|---|---|---|---|
| 1 | Day 0 | — | — | Day 28 | Day 35 |
| 2 | Day 0 | Day 14 | — | Day 28 | Day 35 |
| 3 | Day 0 | Day 14 | Day 21 | Day 28 | Day 35 |

Results:
(i) Regimen 1

DA specific pathogen-free rats (187-213 g) were obtained from the Central Animal house, University of Newcastle, Newcastle, NSW). Rats (6 per group) were given a single IL dose of killed NTHi as per regimen 1 in table 9, of various dose sizes as shown in Table 10. The killed NTHi was contained in 0.3 mL of PBS. The IT boost was with PBS (group A) or $2 \times 10^7$ killed NTHI (groups B-D). Rats were infected intra-tracheally with 50 μL of PBS containing $5 \times 10^8$ live NTHi. The bacteria recovered from BAL and LH is shown in Table 11.

TABLE 10

Dose sizes tested in regimen 1

| Rat group | IL immunization | IT boost |
|---|---|---|
| A | PBS | PBS |
| B | NTHi $3 \times 10^9$ | NTHi $2 \times 10^7$ |
| C | NTHi $3 \times 10^8$ | NTHi $2 \times 10^7$ |
| D | NTHi $3 \times 10^7$ | NTHi $2 \times 10^7$ |

TABLE 11

Recovery of live NTHi from the lung:

| Rat group | BAL CFU ($10^6$) | LH CFU ($10^6$) |
|---|---|---|
| A (5) | 1.12 ± 0.20 | 17.1 ± 1.9 |
| B (6) | 0.76 ± 0.14 P = 0.029* | 8.0 ± 1.5 P = 0.042* |
| C (6) | 0.70 ± 0.20 P = 0.030* | 5.2 ± 1.4 P = 0.006* |
| D (6) | 1.76 ± 0.37 | 16.1 ± 4.7 |

*compared to group D
*compared to group A

It is apparent that for a single immunizing IL-dose both the higher dose levels ($3 \times 10^8$ and $3 \times 10^8$) were equally effective in providing protective immunity. The lowest dose ($3 \times 10^7$) was ineffective.
(ii) Regimen 2

DA specific pathogen-free rats (187-219 g) were obtained from the Central Animal house, University of Newcastle, Newcastle, NSW). Rats (6 per group) were given a single IL dose of killed NTHi as per regimen 2 in table 9, fvarious dose sizes as shown in Table 12. The killed NTHi was contained in 0.3 mL of PBS. The IT boost was with PBS (group A) or $2 \times 10^7$ killed NTHI (groups B-D) in 50 μL of PBS. Rats went infected intra-tracheally with 50 μL of PBS containing $5 \times 10^8$ live NTHi. The bacteria recovered from BAL and LH is shown in Table 13.

TABLE 12

Dose sizes tested in regimen 2

| Rat group | IL dose | Oral dose | IT boost | Infect/kill |
|---|---|---|---|---|
| A | PBS | PBS | PBS | NTHi $3 \times 10^8$ |
| B | NTHi $3 \times 10^7$ | NTHi $3 \times 10^7$ | NTHi $8 \times 10^7$ | NTHi $3 \times 10^8$ |
| C | NTHi $3 \times 10^8$ | NTHi $3 \times 10^8$ | NTHi $8 \times 10^7$ | NTHi $3 \times 10^8$ |
| D | NTHi $3 \times 10^9$ | NTHi $3 \times 10^9$ | NTHi $8 \times 10^7$ | NTHi $3 \times 10^8$ |
| Day | 0 | 14 | 28 | 35 |

TABLE 13

Recovery of live bacteria from the lung:

| Rat group | BAL CFU ($10^6$) | LH CFU ($10^6$) | |
|---|---|---|---|
| A (6) | 12.7 ± 4.0 | 44.7 ± 10.0 | |
| B (5) | 2.9 ± 1.3 | 13.5 ± 1.2 | P = 0.019* |
| C (5) | 5.1 ± 3.4 | 17.2 ± 4.7 | P = 0.042* |
| D (6) | 2.9 ± 4.0  P = 0.042* | 15.4 ± 9.8 | P = 0.045* |

*compared to group A.

It is apparent that when two doses are given, all three dose sizes give the same degree of protection in LH. The level of protection is also comparable for the 3 doses in BAL but is only statistically significant for the highest dose in this experiement.
(ii) Regimen 3

DA specific pathogen-free rats (176-213 g) were obtained from the Central Animal house, University of Newcastle, Newcastle, NSW). Rats (6 per group) were given a single IL dose of killed NTHi as per regimen 3 in table 9, of various dose sizes as shown in Table 14. The killed NTHi was contained in 0.3 mL of PBS. The IT boost was with 50 μL of PBS (group A) or $2 \times 10^7$ killed NTHI in 50 μL of PBS (groups B-D). Rats were infected inta-tracheally with 50 μL of PBS containing $5 \times 10^8$ live NTHi. The bacteria recovered from BAL and LH is shown in Table 15.

TABLE 14

Dose sizes tested in regimen 3

| Rat group | IL dose | Oral doses | IT boost | Infect/kill |
|---|---|---|---|---|
| A | PBS | PBS | PBS | NTHi $3 \times 10^8$ |
| B | NTHi $3 \times 10^7$ | NTHi $3 \times 10^7$ | NTHi $8 \times 10^7$ | NTHi $3 \times 10^8$ |
| C | NTHi $3 \times 10^8$ | NTHi $3 \times 10^8$ | NTHi $8 \times 10^7$ | NTHi $3 \times 10^8$ |
| D | NTHi $3 \times 10^9$ | NTHi $3 \times 10^9$ | NTHi $8 \times 10^7$ | NTHi $3 \times 10^8$ |
| Day | 0 | 14 and 21 | 28 | 35 |

TABLE 15

Recovery of live bacteria from the lung:

| Rat group | BAL CFU ($10^6$) | | LH CFU ($10^6$) |
|---|---|---|---|
| A (6) | 2.2 ± 0.7 | | 16.8 ± 8.0 |
| B (6) | 0.48 ± 0.23 | P = 0.045* | 3.3 ± 1.4 |
| C (6) | 0.79 ± 0.21 | | 5.6 ± 1.8 |
| D (6) | 0.45 ± 0.23 | P = 0.042* | 3.7 ± 1.5 |

*Compared to group A

For 3 intestinal doses (one IL plus two by gavage) similar protection is provided by all three dose levels. There is no apparent advantage of three doses over two doses (regimen 2).

From the above data the equivalent dosage for humans is likely to be of the order of $1 \times 10^{12}$ bacteria.

Example 7

Long-Term Immunization with NTHi and L. acidophilus by a single IL Dose.

An experiment was performed to determine the duration of the enhanced protection provided by addition of L. acidophilus. DA specific pathogen-free rats (201-293 g) were obtained from the Central Animal house, University of Newcastle, Newcastle, NSW). Groups of 6 rats were given an IL dose of 0.75 mL of PBS of PBS containing $5 \times 10^8$ killed NTHI or a mixture of $5 \times 10^9$ killed NTHi and $2.5 \times 10^{10}$ live L. acidophilus as shown in Table 16. Rats were IT boosted 14 days later with 50 μK if PBS or PBS containing $5 \times 10^8$ killed NTHi as shown in Table 16. Three months after the IL dose rats were infected intr-tracheally (IT) with $5 \times 10^8$ live NTHi in 50 μL of PBS. Four hours after infection rats-were sacrificed and BAL and LH prepared for determination of total bacteria, measured as described in above examples and expressed as colony forming units (CFU).

TABLE 16

Rat groups: IL dose and IT boost

| Rat group | IL-immunization | IT-boost |
|---|---|---|
| A | PBS | PBS |
| B | NTHi | NTHi |
| C | L. acidophilus | PBS |
| D | NTHi + L. acidophilus | NTHi |

TABLE 17

Live bacteria recovered from the lung:

| Rat group | BAL CFU ($10^6$) | | LH CFU ($10^6$) | |
|---|---|---|---|---|
| A (6) | 6.2 ± 1.3 | | 10.4 ± 1.7 | |
| B (6) | 1.7 ± 0.4 | P = 0.007* | 7.3 ± 1.4 | P = 0.02$^a$ |
| C (6) | 3.0 ± 0.8 | | 18.8 ± 3.9 | |
| D (5) | 2.6 ± 2.0 | | 16.6 ± 8.4 | |

Note:
one rat in group D died during surgery to perform the IL dose.
*compared to group A.
$^a$compared to group C.

Over this 3 month experiment the immunization with NTHi alone was most effective. There is no apparent effect of additional L. acidophilus dosing over this time period.

Although the present invention was described with reference to specific examples and preferred embodiments, it will be understool that variations in keeping with the broad concepts and the spirit of the invention herein described are also contemplated.

The claims defining the invention area as follows:

1. An orally administrable composition for treating non-typable *Haemophilus influenzae* (NTHi) infections of the respiratory tract, consisting of:
   (a) an enteric-coated dose of a probiotic bacteria that induces a Th1type of a cellular immune response, wherein said probiotic bacteria is *Lactobacillus acidophilus* or *Lactobacillus fermentum*; and
   (b) an enteric-coated dose of at least one antigen of a microorganism that causes an infection at a mucosal surface, wherein the microorganism is non-typable *Haemophilus influenzae* (NTHi) and the ratio of the probiotic bacteria to the microorganism is at least about 5:1.

2. The composition according to claim 1, wherein said at least one antigen is a whole microorganism that causes an infection at a mucosal surface.

3. The composition according to claim 2, wherein the whole microorganism is a killed microorganism.

4. The composition according to claim 2, wherein the whole microorganism is a live or live attenuated microorganism.

5. The composition according to claim 2, wherein the antigen is a homogenate or sonicate of the microorganism.

6. The composition according to claim 1, wherein the probiotic bacteria is live.

7. A method of therapeutic treatment of non-typable *Haemophilus influenzae* (NTHi) infections of the respiratory tract, said method comprising administering to a subject requiring such treatment a composition according to claim 1.

8. The method according to claim 7, wherein the composition is administered to a mucosal surface.

9. The method according to claim 8, wherein the mucosal surface is selected from the group consisting of buccal cavity, the respiratory tract, the intestinal tract, and combinations thereof.

10. The method according to claim 7, wherein the composition is administered orally.

11. The method according to claim 7, wherein the composition is a vaccine that is administered in two courses, followed by a booster course.

12. The method according to claim 7, wherein the amount of probiotic bacteria in the composition is from about $1 \times 10^8$ to about $1 \times 10^{12}$.

13. The method according to claim 7, wherein the antigen is a whole killed microorganism, and wherein the amount of microorganism is administered is from $1\times10^8$ to about $1\times10^{12}$.

14. The method according to claim 13, wherein the ratio of whole killed microorganism to the probiotic bacteria is at least about 05:1.

15. The method according to claim 7, wherein said repeated dose of at least one species of probiotic bacteria is administered before or co-administered with said at least one antigen of said microorganism.

16. The method according to claim 7, wherein the administration of said repeated dose of at least one species of probiotic bacteria continues after the cessation of antigen administration.

17. The method according to claim 7, wherein the administration of said repeated dose of at least one species of probiotic bacteria continues after the cessation of antigen administration.

18. The method according to claim 7, wherein the administration of said repeated dose of at least one species of probiotic bacteria continues after the cessation of antigen administration.

19. The composition of claim 1, wherein the mucosal surface is selected from the group consisting of the buccal cavity, the respiratory tract, the intestinal tract and the combinations thereof.

20. The composition of claim 1, wherein the amount of the probiotic bacteria in the composition is from about $1\times10^8$ to about $1\times10^{12}$.

21. The composition of claim 1, wherein the amount of the microorganism in the composition is from about $1'10^8$ to about $1\times10^{12}$.

22. An orally administrable pharmaceutical composition for treating non-typable *Haemophilus influenzae* (NTHi) infections of the respiratory tract, consisting of:
 (a) an enteric-coated dose of a probiotic bacteria that induces a Th1 type of a cellular immune response, wherein said probiotic bacteria is *Lactobacillus acidophilus* or *Lactobacillus fermentum;*
 (b) an enteric-coated dose of at least one antigen of a microorganism that causes an infection at a mucosal surface, wherein the microorganism is a non-typable *Haemophilus influenzae* (NTHi); and
 (c) a pharmaceutically acceptable carrier, adjuvant, solvent or excipient, wherein the ratio of the probiotic bacteria to the microorganism is at least about 5:1.

23. A method of therapeutic treatment of non-typable *Haemophilus influenzae* (NTHi) infections of the respiratory tract, said method comprising administering to a subject requiring such treatment a composition according to claim 22.

24. The method according to claim 23, wherein said repeated dose of at least one species of probiotic bacteria is administered before or co-administered with said at least one antigen of said microorganism.

25. An orally administrable pharmaceutical composition for treating non-typable *Haemophilus influenzae* (NTHi) infections of the respiratory tract, consisting of:
 (a) an enteric-coated dose of a live probiotic bacteria that induces a Th1 type of a cellular immune response, wherein said live probiotic bacteria is *Lactobacillus acidophilus* or *Lactobacillus fermentum;*
 (b) an enteric-coated dose of at least one antigen of a microorganism that causes an infection at a mucosal surface, wherein the microorganism is a non-typable *Haemophilus influenzae* (NTHi); and
 (c) a pharmaceutically acceptable carrier, adjuvant, solvent or excipient, wherein the ratio of the probiotic bacteria to the microorganism is at least about 5:1.

26. A method of therapeutic treatment of non-typable *Haemophilus influenzae* (NTHi) infections of the respiratory tract, said method comprising administering to a subject requiring such treatment a composition according to claim 25.

27. The method according to claim 26, wherein said repeated dose of at least one species of probiotic bacteria is administered before or co-administered with said at least one antigen of said microorganism.

\* \* \* \* \*